(12) United States Patent
Cooper

(10) Patent No.: US 6,448,219 B1
(45) Date of Patent: Sep. 10, 2002

(54) SCENTED POTPOURRI GEL AND METHOD OF MAKING THE SAME

(75) Inventor: Kenneth Cooper, Jacksboro, TN (US)

(73) Assignee: Iced Scents, LLC, Jacksboro, TN (US)

( * ) Notice: Subject to any disclaimer, the term of this patent is extended or adjusted under 35 U.S.C. 154(b) by 0 days.

(21) Appl. No.: 09/503,623

(22) Filed: Feb. 11, 2000

(51) Int. Cl.$^7$ ................................................ A61K 7/46
(52) U.S. Cl. ...................... 512/4; 512/2; 512/3; 516/53; 428/321.5; 428/905; 424/76.4; 424/451; 424/456
(58) Field of Search ........................ 512/2, 3, 4; 516/53; 428/321.5, 905; 424/76.4, 456, 451

(56) References Cited

U.S. PATENT DOCUMENTS

| | | | |
|---|---|---|---|
| 4,071,616 A | * | 1/1978 | Bloch ............................ 424/76 |
| 4,128,507 A | * | 12/1978 | Mitzner .......................... 512/4 |
| 4,137,196 A | * | 1/1979 | Sakurai .......................... 512/4 |
| 4,719,040 A | * | 1/1988 | Traas et al. ..................... 512/4 |
| 5,576,286 A | | 11/1996 | Karp et al. |
| 5,641,847 A | | 6/1997 | Hozumi et al. |
| 5,679,334 A | | 10/1997 | Semoff et al. |
| 5,985,821 A | | 11/1999 | Dobler et al. |

* cited by examiner

Primary Examiner—Jeffrey Snay
Assistant Examiner—Monique T. Cole
(74) Attorney, Agent, or Firm—Pitts & Brittian, P.C.

(57) ABSTRACT

A fragrant potpourri gel mixture is disclosed for dispensing fragrance to the air from a container, with the mixture lacking free liquids and being pourable into or out of the container. The fragrant potpourri gel mixture is prepared by providing an aqueous-based liquid, adding a bittering agent, and combining a coloring agent to form an aqueous-based mixture. An oil-based compound having a volatile fragrance oil component is added to the aqueous-based liquid. An absorbent polymer is mixed in by agitation or stirring to absorb the aqueous-based liquid within a gel mixture and to emulsify the oil-based fragrance component throughout to form a heterogeneous gel mixture having a plurality of micro-droplets of oil fragrance components and air pockets suspended therein. The heterogeneous gel mixture is prepared at room temperatures without heating. The volatile fragrance components of the micro-droplets volatilize from the surfaces of the micro-droplets when exposed to the air. To improve the release of volatile fragrance component, a petroleum solvent is mixed with the oil-based compound added to the aqueous-based liquid mixture. Also disclosed is a method of making a fragrant potpourri gel that includes producing a heterogeneous gel mixture having a plurality of micro-droplets of oil fragrances and air pockets therein, each of the micro-droplets releasing volatile oil-based fragrance to the air when the container is opened.

20 Claims, 1 Drawing Sheet

SCENTED POTPOURRI GEL AND METHOD OF MAKING THE SAME

BACKGROUND OF INVENTION

1. Field of Invention

Figure 1:
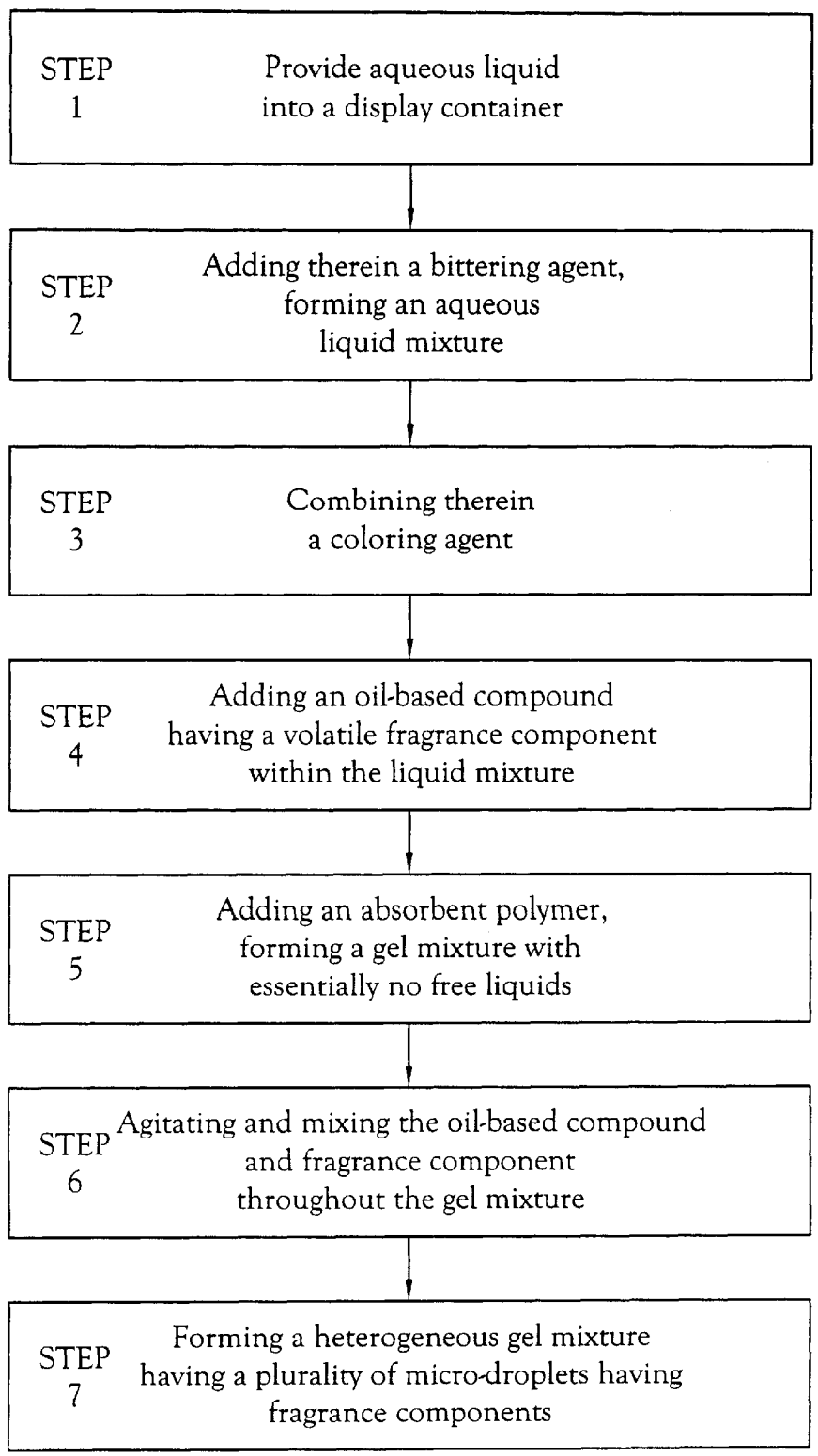

The invention relates to a semi-solid mixture of fragrant components and a method of making the semi-solid mixture. More specifically, the invention relates to a mixture of fragrant components, additives, and absorbents in a gelatinous mixture and a method of making the gelatinous mixture.

2. Description of the Related Art

Fragrant mixtures of solid and liquid components are available in the form of solids, semi-solids, or liquid mixtures for adding fragrance to the air or the skin of a user. A liquid containing fragrant mixtures of compounds can be formed into a gelatinous mixture by evaporating the liquid to increase the viscosity, or by increasing the proportion of solids within the mixture to absorb the liquid portion and to form a colloidal mixture. A gelatinous mixture, also referred to as a gel mixture in the following disclosure, is a viscous mixture of components in a colloidal, semi-solid form having no free liquids. Fragrant mixtures of components having a potpourri of fragrances are heated by an external heating unit or by a candle for delivery of the fragrances into the air by evaporation. Prior known fragrance mixtures may contain components that are flammable and/or toxic, and may separate into layers if the mixtures are not agitated frequently. The prior fragrance mixtures known in the art may evaporate unevenly, providing initially rapid evaporation rates and high fragrance concentrations, with diminishing evaporation rates and low fragrance concentrations after prolonged exposures to the air of the mixtures.

Typical of the prior art are those potpourri fragrance mixtures disclosed in the following U.S. Patents. U.S. Pat. No. 5,985,821, issued to Dobler, et al., discloses a spreadable fragrance gel including about 10% to 20% fragrance oil, and about 80% to 85% alcohol, blended with about 5% polymer to increase the viscosity of the mixture to minimize pouring from a container. The spreadable fragrance gel is designed to absorb into the skin of a user.

U.S. Pat. No. 5,679,334, issued to Semoff, et al., discloses a transparent aqueous gel air freshener including volatile microemulsified fragrance oil, water, gelling agent, co-solvent, aversive agent and cross-linking agent. The aqueous gel composition further includes a cationically cross-linked modified polysaccharide, and the gel composition being free of visible particles and inhomogeneities. The gel composition includes color and ornamental botanical materials suspended within the gel composition, such as berries, slices of fruit, leaves, seeds, flowers, sprigs, branchlets and Queen Anne's lace. The gel composition may be prepared by combining the components at temperatures above 40° C., and cooling the components to about 38° C. to about 40° C. while adding botanical materials, to form the gel composition in a container having the desired viscosity and clarity.

U.S. Pat. No. 5,641,847, issued to Hozumi, et al., discloses a gel-like aromatic agent incorporated into a oil-absorbent, swelling cross-linked polymer, with the aromatic component consisting of jasmine oil, citric oils, or synthetic perfume for improving the aroma in a space. The gel-like aromatic agent is formed by polymerization of a monomer component to form a cross-linked polymer possessing at least one polymerizable unsaturated group in the molecular unit for incorporation of the aromatic component in the polymer.

U.S. Pat. No. 5,576,286, issued to Karp, et al., discloses a liquid potpourri solution including water, hydroxypropylcellulose, polymer of acrylic acid cross-linked with allyl ethers of pentaerythritol or allyl ethers of sucrose, and water soluble polymer encapsulated fragrance droplets. The pH of the potpourri solution is adjusted to form a liquid potpourri which releases fragrance only upon the application of heat. The potpourri solution undergoes chemical reactions upon adjustment of the pH and heating to form the required polymer matrix, which requires heating for release of fragrance.

Accordingly, there is a need for an improved fragrance product that provides a semi-solid mixture of a potpourri of fragrances that releases the fragrances in a gradual, long-lasting, controlled manner without drying of the exposed layers of the mixture when exposed to the air at temperatures of about 21.1° C. (about 70° F.).

Therefore, it is an object of the present invention to provide an aromatic mixture in a semi-solid form that emits fragrance when exposed to air.

It is another object of the present invention to provide a containerized potpourri gel that, when exposed to air, allows fragrance to volatilize over an extended period of time.

It is another object of the present invention to provide a method of making a potpourri gel that contains fragrance oils dispersed throughout an aqueous gel matrix without the presence of free liquids.

It is another object of the present invention to provide a method of making a potpourri gel that contains fragrance oils absorbed in micro-droplets co-mingled throughout an absorbent polymer that is pourable into containers.

BRIEF SUMMARY OF INVENTION

A fragrant potpourri semi-solid mixture is disclosed for dispensing fragrance to the air from a container, with the mixture lacking free liquids and being pourable into or out of the container without heating of the mixture. Also, a method for making the potpourri semi-solid mixture is disclosed. The fragrant potpourri semi-solid mixture includes an aqueous-based liquid to which is added a bittering agent and a coloring agent within a display container. An oil-based fragrance compound including a volatile fragrance oil component is mixed with the aqueous-based liquid, bittering agent, and coloring agent to form a aqueous-based mixture. An absorbent polymer is added to the mixture and the mixture is agitated or stirred to suspend the oil-based fragrance component in a plurality of micro-droplets dispersed throughout the mixture to form an heterogeneous gel mixture. The absorbent polymer absorbs the aqueous-based liquid, bittering agent, and coloring agent to effectively minimize free liquids in the gel mixture. The gel mixture containing the absorbent polymer forms the heterogeneous gel mixture that is mixed with the plurality of micro-droplets containing oil-based fragrance components that are separate from, and not chemically combined with, the aqueous-based component of the absorbent polymer. The gel mixture includes a plurality of air pockets dispersed therein, with the fragrance oil micro-droplets dispersed evenly throughout the gel mixture. The heterogeneous gel mixture is viscous and pourable from one display container to another container at temperatures of about 21.1° C. (about 70° F.), without heating. To encourage volatilization of the oil-based fragrance components, the heterogeneous gel mixture can be mixed with a non-flammable petroleum solvent that is odorless and combines with the micro-droplets of volatile fragrance oil components to increase the evaporation of the volatile fragrance oil components from the micro-droplets of the gel mixture when exposed to the air by opening of the display container.

Also disclosed is a method of making a potpourri gel for dispensing fragrance to the air from a container, comprising providing an aqueous-based liquid, adding a bittering agent and combining a coloring agent with the aqueous-based liquid to form an aqueous liquid mixture within the container. The method includes adding an oil-based compound having a volatile fragrance component to the aqueous-based liquid mixture. An absorbent polymer is added and the mixture is agitated, with absorbing of the aqueous-based liquid mixture by the absorbent polymer during agitating or stirring. A gel mixture is formed having essentially no free liquids. The method emulsifies the oil-based compound having the volatile fragrance components throughout the gel mixture within a plurality of micro-droplets that are external to, and not chemically combined with, the aqueous-based gel mixture. A plurality of air pockets are distributed throughout the gel mixture during the agitating or stirring operations. The heterogeneous gel mixture can be poured into one or more display containers at room temperatures of about 21.1° C. (about 70° F.). The oil-based fragrance compound within each micro-droplet in the gel mixture includes volatile fragrance components which are released in a gradual evaporation process when the gel mixture is exposed to the air.

BRIEF DESCRIPTION OF SEVERAL VIEWS OF DRAWINGS

The above-mentioned objects and advantages of the present invention are readily apparent from the description of the invention contained herein, and by reference to the claims, read together with the drawing in which FIG. 1 is a schematic of the method of making of a fragrant potpourri gel mixture of the present invention.

DETAILED DESCRIPTION OF THE INVENTION

In accordance with the present invention, there is disclosed a semi-solid mixture for dispensing fragrance to the air from a container, and a method of making the mixture as depicted in FIG. 1. The semi-solid mixture is an improved scented potpourri gel that includes a combination of components that form a gel mixture having an aqueous-based liquid portion absorbed within absorbent polymers, and having oil-based compounds having volatile fragrance components in a plurality of micro-droplets emulsified throughout the heterogeneous gel mixture.

The gel mixture is prepared by providing an aqueous-based liquid such as water (first step of FIG. 1), to which a bittering agent is added (second step of FIG. 1), and to which a coloring agent is added (third step of FIG. 1), preferably in a display container that can be of any appropriate volume to provide a two to three month supply of fragrant potpourri gel mixture.

An aversive agent or bittering agent of the second step includes a nontoxic substance may be combined in the gel mixture to add a bitter or unpleasant taste to the mixture. A sufficient amount of bittering agent is combined with the gel mixture to provide a bitter taste to minimize the ingestion of the gel mixture that may pose health hazards for children. One such aversive agent is Bitrex (dentantonium benzoate). The coloring agent of the third step can be any appropriate chemical compound known to one skilled in the art that provides a preferred color to the aqueous-based liquid.

In the fourth step of FIG. 1, a volume of oil-based compounds having at least one volatile fragrance component is added to the aqueous-based liquid. The emulsified portions of the volume of oil-based compound form a plurality of droplets such as beads or micro-droplets which are dispersed throughout the mixture but do not chemically react with the aqueous-based liquid, the bittering agent, or the coloring agent. Each micro-droplet of the plurality of droplets includes an amount of the oil-based compound having at least one volatile fragrance component, therefore the micro-droplets are separate entities dispersed throughout the aqueous-based liquid. The oil-based compound can be mixed in with the aqueous-based liquid in a ratio of approximately 0.5 ounce of oil-based compound to approximately 12 ounces of the mixture of aqueous-based liquid, bittering agent, and coloring agent. Alternatively, the ratio is approximately 1 part of oil-based compound to approximately 25 parts of the mixture of aqueous-based liquid. The volatile fragrance components of the oil-based compound may be a combination of a plurality of organic compounds that volatilize at different rates upon exposure to the air. The volatile fragrance components can include aromas of fruits, pine trees, baked foods, and/or any variety of aromas that are chemically reproducible by one skilled in the art. The volatile fragrance component can have highly volatile fractions and less volatile fractions that have typical vapor pressures of between approximately 0.2 mm Hg to approximately 20 mm Hg at 20° C. (68° F.). The volatile fragrance components do not include significant amounts of alcohol.

In the fifth step of FIG. 1, an absorbent polymer is combined with, and absorbs the aqueous-based liquid, bittering agent, and coloring agent thereby forming a gel mixture includes essentially minimal free liquids. The absorbent polymer is mixed with the aqueous-based liquid in a ratio of approximately 300 parts of liquid to approximately 1 part polymer. In a preferred embodiment, the absorbent polymer is mixed in a ratio of approximately 150 parts of liquid to approximately 1 part polymer.

The absorbent polymer can be selected from any of the group of absorbents including AquaSorbe®-HP superabsorbent polymer, manufactured by Aquadox of Romeoville, Ill, or Quik-Solid®, polyacrylate superabsorbent polymer, manufactured by Colloid Environmental Technologies Company of Arlington Heights, Ill., or absorbent compounds containing cross-linked sodium polyacrylate and acrylic acid, or other similar absorbent compounds having polymer components. Alternative absorbents preferably are not biodegradable and are germicidal.

After adding the absorbent polymer to the mixture, the sixth step includes an agitation means for agitating the gel mixture by a stirring or shaking device to suspend the oil-based compound and volatile fragrance components within a plurality of droplets that are uniformly emulsified throughout the gel mixture. After adequate agitation, step seven includes forming a heterogeneous gel mixture including a plurality of immiscible, fragrance containing micro-droplets therein. The immiscible droplets are composed of hydrophobic oil-based compounds, that are bond together by hydrophobic bonding of polar groups to form micro-droplets within an aqueous-based gel matrix provided by the aqueous-based liquid and the absorbent polymer. The immiscible droplets can include mini-droplets, micro-spheres, or small polyhedral shaped micro-droplets composed of oil-based compounds and fragrance components. The fragrance containing micro-droplets can be re-dispersed throughout the heterogeneous gel mixture by agitation, stirring, or shaking of the container if the gel mixture remains within the container for long periods of storage. As the aqueous portion of the heterogeneous gel mixture evaporates when exposed to air, the immiscible, fragrance containing micro-droplets become exposed to the air at the surface of the gel mixture. Due to the large surface area presented by the plurality of fragrance containing micro-droplets, when the micro-droplets are exposed to the air at or near the external surface of the gel mixture, the evaporation of the volatile fragrance component from each micro-droplet is rapid.

An optional step after step 5 of FIG. 1 can include mixing a volatile solvent to the heterogeneous gel mixture and agitating the container by stirring or shaking in step 6. The volatile solvent being added is a non-flammable, petroleum based solvent that is volatile with a vapor pressure of approximately 0.2 mm Hg at 20° C., and having essentially clear coloration. The addition of the volatile solvent provides a highly volatile fraction absorbed into the fragrance containing micro-droplets, therefore increasing the volatilization of the volatile fragrance component from each micro-droplet within the heterogeneous gel mixture.

After preparing the heterogeneous gel mixture within the display container by the steps of FIG. 1, an opened container can be placed in a convenient location to allow evaporation of the volatile fragrance component without the addition of heat. The gel mixture does not have to be heated for releasing of the volatile fragrance component and dispensing of the fragrance from the mixture to permeate the air throughout the area around the open display container. During volatilization, the gel mixture retains residual amounts of oil-based compounds in fragrance containing micro-droplets emulsified within the heterogeneous gel mixture. Th e residual amounts of oil-based compounds in the micro-droplets can be redistributed throughout the gel mixture by additional agitating by stirring or shaking of the closed container. External heat can also be applied to the gel mixture to volatilize the residual amounts of fragrance components.

The multi-surfaced droplets also provide an aesthetically pleasing sparkling light effect to the heterogeneous gel mixture. At each surface interface between the aqueous-based liquids bound by the absorbent polymer, and the oil-based containing micro-droplets within the gel mixture, external light is diffracted and diffused within the gel mixture and reflected out wards from the gel mixture, thereby providing a sparkling light effect.

Evaporation of the volatile fragrance component from the heterogeneous gel mixture is assisted by a plurality of air pockets formed throughout the gel mixture during agitation by stirring or shaking of the gel mixture. The plurality of air pockets provide additional pathways through the gel mixture for volatile fragrance components to diffuse from the micro-droplets and toward the surface of the gel mixture exposed to the air, therefore increasing an opportunity for evaporation of volatile fragrance components.

An additional factor assisting the evaporation of the volatile fragrance component from the heterogeneous gel mixture is that the gel mixture, once formed in a display container, includes a plurality of surfaces of the fragrance containing micro-droplets that potentially become exposed to the air. The increased surface area of the plurality of fragrance containing micro-droplets allows for rapid evaporation of volatile fragrance components from the heterogeneous gel mixture when exposed to air at normal room temperatures, without the addition of heat.

Agitating and mixing of the gel mixture in the display container by stirring or shaking allows for emulsifying of the micro-droplets throughout the heterogeneous gel mixture. The heterogeneous gel mixture is pourable from one container to another display container at room temperatures of about 21.1° C. (about 70° F.), without the addition of external heating. The heterogeneous gel mixture having dispersed micro-droplets therein conforms to the shape of the display container and maintains the plurality of air pockets formed during stirring or shaking, to provide additional evaporation pathways through the gel mixture. A plurality of interfaces exist within the gel mixture between the micro-droplets emulsified throughout the aqueous-based liquids absorbed by the adsorbent polymer. The plurality of surfaces of the plurality of micro-droplets within the gel mixture allow for rapid evaporation of volatile fragrance components from the gel mixture when the surfaces of each fragrance containing micro-droplet are exposed to the air.

After repeated and/or prolonged exposure of external surfaces to the air, the more volatile fragrance components in the micro-droplets become depleted. To extend the evaporation of fragrance components from the gel mixture after extended exposure to the air, the gel mixture within the container can be agitated by shaking or stirring to re-distribute the micro-droplets throughout the gel mixture. As an alternative, during the step of adding an oil-based compound having a volatile fragrance component, a solvent or co-solvent can be added along with the oil-based compound in the form of a volatile liquid such as a petroleum solvent. The added volatile liquid solvent is preferably odorless and non-flammable, and can be stirred into the gel mixture, with agitation provided by the operator or an agitation machine known to one skilled in the art, to disperse the additional volatile liquid solvent throughout the gel mixture. One alternative solvent is Isopar-M, a petroleum distillate that is predominantly composed of isoparaffinic hydrocarbons (Carbon 12 to Carbon 15), with a vapor pressure of about 0.2 mm Hg at 20° C. (68° F.). Alternatives to Isopar-M, include Isopar-H or Isopar-L, or similar solvents that have high vapor pressure, odorless, and non-flammable properties. The added volatile liquid solvent dissolves within the micro-droplets within the gel mixture and provides for improved evaporation rates of the volatile fragrance components from the micro-droplets.

A method of making a potpourri gel that dispenses fragrance to the air from a container is disclosed, the method including the operation of making a heterogeneous gel mixture by providing an aqueous-based liquid in a display container in a first step as outlined in FIG. 1. A second step includes adding a bittering agent to the aqueous-based liquid. A third step includes combining a coloring agent with the aqueous-based liquid and the bittering agent in the display container, forming an aqueous-based liquid mixture. A fourth step includes adding a volume of oil-based compounds, each having a volatile fragrance component, within the aqueous-based liquid mixture. The adding step forms a suspension of the oil-based compounds having a volatile fragrance component in the aqueous-based liquid mixture.

A fifth step includes combining an absorbent polymer to the aqueous-based liquid mixture, with the absorbent polymer absorbing the aqueous-based liquids, forming a matrix referred to hereafter as the gel mixture of the current invention. The oil-based compounds remain physically separate from the gel matrix, without chemically reacting with the aqueous-based liquids or the absorbent polymer of the gel mixture, but can be dispersed throughout the gel mixture.

A sixth step includes agitating the gel mixture by stirring and/or shaking the gel mixture confined with in the display container. The agitating step further includes emulsifying the oil-based compounds within the gel mixture, forming and dispersing a plurality of micro-droplets containing the oil-based compounds throughout the gel mixture. Each micro-droplet preferably includes a portion of the oil-based compounds having a fragrance component. The agitating step forms an heterogeneous gel mixture having the plurality of micro-droplets dispersed throughout the gel mixture, with essentially no free liquids remaining in the display container because the aqueous-based liquids, bittering agent, and coloring agent are absorbed with the absorbent polymer. The first through sixth steps do not require the addition of heat to assist the emulsifying step or the agitating step. Further, the first through sixth steps can proceed at room temperature, about 21.1° C. (about 70° F.).

As an alternative operation, a step is added to the emulsifying step by adding a volatile solvent having odorless and non-flammable properties to the gel mixture for combining with the oil-based compounds throughout the gel mixture. The agitating step provides mixing of the volatile solvent and oil-based compounds to form a heterogeneous gel mixture having a plurality of fragrance containing, micro-droplets distributed therein. The volatile solvent is preferably petroleum based, and volatile with a vapor pressure of approximately 0.2 mm Hg at 20° C. The volatile solvent can be clear in coloration or colored. The volatile solvent adds a highly volatile fraction to each micro-droplet, therefore assisting with the volatilization of the volatile fragrance component from each micro-droplet within the heterogeneous gel mixture when exposed to the air.

The heterogeneous gel mixture includes a plurality of air pockets distributed therein during the agitating step. The heterogeneous gel mixture releases the volatile fragrance components at a vapor pressure great enough to volatilize the fragrance at ambient room temperature, about 21.1° C. (about 70° F.), without heating. Heating the heterogenous gel mixture increases evaporation rates of volatile fragrance components.

One skilled in the art will recognize alternative polymer compounds with comparable aqueous-liquid absorbing properties, and alternative volatile solvents and fragrance components that can be utilized within the gel mixture to provide embodiments of the scented potpourri gel with different scents and colors.

From the foregoing description, advantages will be recognized by those skilled in the art for the semi-solid mixture comprising a gel mixture of volatile fragrances, and method of making of the present invention. One advantage is that the scented potpourri gel does not contain significant concentrations of alcohol and therefore is not highly flammable. Another advantage is that the gel mixture does not have to be heated to release the fragrance components to the air. The scented potpourri gel can be mixed with appropriate volatile fragrance components, and coloring agents to form a gel mixture that is pleasing to the smell and pleasing to the look of the consumer. The bittering agent mixed with the gel mixture reduces the risk of a child's consumption of the pleasant smelling mixture. The gel mixture contains minimal free liquids and does not spill liquids when tipped over. The gel mixture is fluid at temperatures of about 21.1° C. (about 70° F.), to allow the gel mixture to pour from one display container to another display container. The scent and/or evaporation rates of the fragrance components of the potpourri gel can be modified by the addition of volatile solvents prior to the agitating step.

While a preferred embodiment is shown and described, it will be understood that it is not intended to limit the disclosure to the embodiments of the invention described, but rather it is intended to cover all modifications and methods falling within the spirit and scope of the invention as defined in the appended claims. One skilled in the art will recognize related alternative embodiments encompassed by the disclosure of the invention contained herein.

What is claimed is:

1. A method for making a potpourri gel for dispensing fragrance to the air from a container, comprising the steps of:
   providing an aqueous-based liquid in a container;
   mixing a bittering agent with said aqueous-based liquid;
   combining a coloring agent with said aqueous-based liquid and said bittering agent, wherein an aqueous liquid mixture is formed;
   adding oil-based compounds having a volatile fragrance component to said aqueous liquid mixture, in a ratio of about 1 part of oil-based compounds having a volatile fragrance component to about 12 parts of said aqueous-based liquid, said step of adding said oil-based compounds having a volatile fragrance component dispersing oil-based compounds having a volatile fragrance component evenly throughout said aqueous liquid mixture;
   adding an absorbent polymer with said aqueous liquid mixture;
   agitating said absorbent polymer with said aqueous liquid mixture, said absorbent polymer absorbing said aqueous liquid mixture, said agitating step forming a gel mixture being essentially free of uncombined liquids in the container; and
   forming a plurality of micro-droplets during said agitating step, each of said plurality of micro-droplets including a portion of oil-based compounds having a volatile fragrance component, said agitating step emulsifying and dispersing said plurality of micro-droplets throughout said gel mixture.

2. The method of claim 1, wherein said step of adding oil-based compounds having a volatile fragrance component further comprises adding a volatile liquid solvent to said gel mixture, said step of adding a volatile liquid solvent including combining said volatile liquid solvent into each of said plurality of micro-droplets.

3. The method of claim 2, wherein said step of adding a volatile liquid solvent further comprises adding said volatile liquid solvent having a vapor pressure of about 0.2 mm Hg at 20° C.

4. The method of claim 3, wherein said steps proceed at ambient room temperature of about 21.1° C., without heating of said gel mixture.

5. The method of claim 4, wherein said step of adding an absorbent polymer further comprises adding absorbent polymer with said aqueous liquid mixture in a ratio of about 300 parts aqueous liquid mixture to about 1 part absorbent polymer.

6. The method of claim 4, wherein said step of adding an absorbent polymer further comprises adding absorbent polymer with said aqueous liquid mixture in a ratio of about 150 parts liquid to about 1 part absorbent polymer.

7. The method of claim 1, wherein said step of adding oil-based compound having a volatile fragrance component further comprises adding oil-based compounds having a volatile fragrance component in a ratio of about 25 parts aqueous liquid mixture to about 1 part oil-based compounds having a volatile fragrance component.

8. A semi-solid mixture for dispensing fragrance to the air from a container, comprising:

a solution including:
   an aqueous-based liquid;
   a bittering agent; and
   a coloring agent;
an oil-based compound having a volatile fragrance component, said oil-based compound having a volatile fragrance component dispersed within said solution in a ratio of about 1 part of said oil-based compound having a volatile fragrance component to about 12 parts of said solution;
an absorbent polymer dispersed within said solution and said oil-based compound having a volatile fragrance component, whereby said solution is absorbed by said absorbent polymer in a gel mixture that is essentially free of uncombined liquids; and
a plurality of micro-droplet formed in said gel mixture, said plurality of micro-droplets throughout said gel mixture, each of said plurality of micro-droplets contains a portion of said oil-based compound having a volatile fragrance component;
whereby said volatile fragrance component within each of said plurality of micro-droplets is evaporated from said gel mixture when said gel mixture is exposed to the air.

9. The semi-solid mixture of claim 8, further comprising a volatile liquid solvent being mixed with said oil-based compound having a volatile fragrance component in said gel mixture, said volatile liquid solvent dispersed in said plurality of micro-droplets within said gel mixture.

10. The semi-solid mixture of claim 9, wherein said volatile liquid solvent is a non-flammable petroleum solvent.

11. The semi-solid mixture of claim 10, wherein said volatile liquid solvent is a volatile compound having a vapor pressure in the range of about 0.2 mm Hg to about 20 mm Hg at 20° C.

12. The semi-solid mixture of claim 8, wherein said absorbent polymer is dispersed within said solution in a ratio of about 300 parts of said solution to about 1 part of said absorbent polymer.

13. The semi-solid mixture of claim 8, wherein said absorbent polymer is dispersed within said solution in a ratio of about 150 parts of said solution to about 1 part of said absorbent polymer.

14. The semi-solid mixture of claim 8, wherein said oil-based compound having a volatile fragrance component being emulsified into said solution in a ratio of about 25 parts of said solution to about 1 part of said oil-based compound having a volatile fragrance component.

15. The semi-solid mixture of claim 8, wherein said oil-based compound having a volatile fragrance component further comprises a plurality of volatile fragrance components having vapor pressures in the range of about 0.2 mm Hg to about 20 mm Hg at 20° C.

16. In a scented potpourri mixture including an aqueous liquid containing a bittering agent and a coloring agent,
   wherein the improvement comprising:
      an emulsion of an oil-based compound having a volatile fragrance component emulsified throughout the aqueous liquid containing the bittering agent and the coloring agent, said emulsion includes a plurality of fragrance containing micro-droplets dispersed in the aqueous liquid containing the bittering agent and the coloring agent;
      an aqueous-absorbent polymer added to absorb the aqueous liquid containing the bittering agent and the coloring agent; and
      a gel mixture formed by said aqueous-absorbent polymer added to the aqueous liquid containing the bittering agent and the coloring agent, said gel mixture being essentially free of uncombined liquids, whereby said plurality of fragrance containing micro-droplets are dispersed throughout said gel mixture.

17. The scented potpourri mixture of claim 16, further comprising a volatile liquid added to said gel mixture, said volatile liquid including a non-flammable petroleum solvent, said volatile liquid dispersed in said fragrance containing micro-droplets, said volatile fragrance component and said volatile liquid evaporates from said micro-droplets within said gel mixture when exposed to the air.

18. The scented potpourri mixture of claim 16, wherein said aqueous-absorbent polymer being added to said aqueous liquid containing the bittering agent and the coloring agent in a ratio of about 300 parts liquid to about 1 part aqueous-absorbent polymer.

19. The scented potpourri mixture of claim 16, wherein said oil-based compound having a volatile fragrance component being added to said aqueous liquid containing the bittering agent and the coloring agent is emulsified into said gel mixture in a ratio of about 12 parts gel mixture to about 1 part oil-based compound having a volatile fragrance component.

20. The scented potpourri mixture of claim 19, wherein said volatile fragrance component includes a vapor pressure in the range of about 0.2 mm Hg to about 20 mm Hg at 20° C.

* * * * *